(12) United States Patent
Terada et al.

(10) Patent No.: US 8,425,939 B2
(45) Date of Patent: Apr. 23, 2013

(54) REMEDY

(75) Inventors: Hiroshi Terada, Tokyo (JP); Kimiko Makino, Kanagawa (JP); Gen-Ichiro Soma, Tokyo (JP)

(73) Assignee: Hiroshi Terada, Tokyo (JP)

( * ) Notice: Subject to any disclaimer, the term of this patent is extended or adjusted under 35 U.S.C. 154(b) by 0 days.

(21) Appl. No.: 12/659,796

(22) Filed: Mar. 22, 2010

(65) Prior Publication Data

US 2010/0178354 A1 Jul. 15, 2010

Related U.S. Application Data

(62) Division of application No. 10/525,964, filed as application No. PCT/JP03/10871 on Aug. 27, 2003, now abandoned.

(30) Foreign Application Priority Data

Aug. 27, 2002 (JP) .................................. 2002-247871

(51) Int. Cl.
 *A61K 9/14* (2006.01)
(52) U.S. Cl.
 USPC ........................................................ 424/489
(58) Field of Classification Search .................. None
 See application file for complete search history.

(56) References Cited

U.S. PATENT DOCUMENTS

| | | | |
|---|---|---|---|
| 1,739,064 A | 12/1929 | Dickerson | |
| 5,346,891 A | 9/1994 | Soma et al. | |
| 5,494,819 A | 2/1996 | Soma et al. | |
| 5,759,583 A | 6/1998 | Iwamoto et al. | |
| 6,248,345 B1 | 6/2001 | Goldenheim et al. | |
| 2002/0106461 A1 | 8/2002 | Talton | |
| 2002/0164290 A1* | 11/2002 | Stefely et al. | 424/45 |

FOREIGN PATENT DOCUMENTS

| | | |
|---|---|---|
| JP | 11-116498 A | 4/1999 |
| JP | 2000-186040 A | 7/2000 |
| WO | WO-00/28969 A2 | 5/2000 |

OTHER PUBLICATIONS

Office Action mailed Feb. 15, 2008, issued by State Intellectual Property Office of the PRC (China) for the Chinese Patent Application No. 2006101149254.
S. Goto et al., "Intradermal administration of lipopolysaccharide in treatment of human cancer," Cancer Immunology, Immunotherapy, 1996, vol. 42, No. 4, pp. 255-261.
Chinese Office Action mailed May 9, 2008, issued from the China Patent Office and its partial translation.
Chinese Office Action mailed Aug. 29, 2008, issued from the China Patent Office and its partial translation.
Zhou Feng-li et al., "Alveolar Macrophage Producing Cell Factors and Killing Cells in Patients with Lung Cancer," Chinese Journal of Cancer, 20(9); 2001; pp. 929-931.
P. O'Hara, et al; "Respirable PLGA microspheres containing rifampicin for the treatment of tuberculosis: manufacture and characterization;" Pharm. Res.; vol. 17; No. 8; 2000; pp. 955-961./Discussed in the specification.

(Continued)

*Primary Examiner* — Paul Dickinson
(74) *Attorney, Agent, or Firm* — Edwards Wildman Palmer LLP

(57) ABSTRACT

It is intended to provide a remedy for diseases caused by macrophages with dysfunction or mediated by macrophages. Namely, a remedy which activates the phagocytic capacity of macrophages and thus is efficiently incorporated into the macrophages due to the vigorous phagocytosis. As a result, the macrophages with dysfunction are normalized, macrophages infected with a pathogen are exterminated or a pathogen in the infected macrophages is exterminated.

1 Claim, 7 Drawing Sheets

OTHER PUBLICATIONS

R. Sharma, et al.; "Inhalable microparticles containing drug combinations to target alveolar macrophages for treatment of pulmonary tuberculosis;" Pharm. Res.; vol. 18; No. 10; 2001; pp. 1405-1410./ Discussed in the specification.

E.L. Barrow, et al; "Use of microsphere technology for targeted delivery of rifampin to *Mycobacterium tuberculosis*-infected macrophages;" Antimicrobal Agents and Chemotherapy; vol. 42; No. 10; 1998; pp. 2682-2689.

Hickey, J. A., et al.; "Efficacy of Rifampicin-Poly(Lactide-Co-Glycolide) Microspheres in Treating Tuberculosis;" Respiratory Drug Delivery VI; pp. 201-209. (1998).

Takahashi, K. et al. "Life-Supporting Macrophages;" Bunkodo; pp. 141-146 (2001); and English translation.

Suarez, S., et al. "Respirable PLGA Microspheres Containing Rifampicin for the Treatment of Tuberculosis: Screening in an Infectious Disease Model;" Pharmaceutical Research; vol. 18, No. 9, pp. 1315-1319 (2001), and cover sheets (2 sheets).

Prior, S., et al. "In vitro phagocytosis and monocyte-macrophage activation with poly(lactide) and poly(lactide-co-glycolide) microspheres;" European Journal of Pharmaceutical Sciences; vol. 15, pp. 197-207 (2002), and cover sheets (2 sheets).

Matsuyama. T., et al. "Cytocidal Effect of Tumor Necrosis Factor on Cells Chronically Infected with Human Immunodeficiency Virus (HIV): Enhancement of HIV Replication;" Journal of Virology; vol. 63, No. 6, pp. 2504-2509 (1989).

Pushkarsky, T., et al. "Lipopolysaccharide stimulates HIV-1 entry and degradation in human macrophages;" Journal of Endotoxin Research; vol. 7, No. 4, pp. 271-276 (2001).

Matsumoto, N., et al. "ONO-4007, an Antitumor Lipid A Analog, Induces Tumor Necrosis Factor-α Production by Human Monocytes Only under Primed State: Different Effects of ONO-4007 and Lipopolysaccharide on Cytokine Production;" The Journal of Pharmacology and Experimental Therapeutics; vol. 284, No. 1, pp. 189-195 (1998).

S. Suarez et al.; "Airways delivery of rifampicin microparticles for the treatment of tuberculosis," Journal of Antimicrobial Chemotherapy; vol. 48, No. 3; 2001; pp. 431-434 and cover page.

H. Inagawa et al.; "Anti-tumor Effect of Lipopolysaccharide by Intradermal Administration as a Novel Drug Delivery System;" Anticancer Research; vol. 17; 1997; pp. 2153-2158.

H. Inagawa et al.; "Antitumor Mechanism of Intradermal Administration of Lipopolysaccharide;" Anticancer Research; vol. 17; 1997; pp. 1961-1964 and cover page.

G-I. Soma; "Dynamic Aspects of Cytokine Network to Induce Antitumor Effects by Intradermal Administration of Low Molecular Weight Lipopolysaccharide Derived from *Pantoea agglomerans*;" Advances in Pharmaceutical Sciences; vol. 16; 2000; Japan; pp. 7-22 and publisher info. page. / partial translation is attached (3 sheets).

H. Kasugai; "Experimental study of antitumor effetc of lipopolysaccharide extracted from *Pantoea agglomerans*;" Teikyo Medial Journal; vol. 21; No. 5; 1998; Japan; pp. 389-402 and publishe info. page. / partial translation is attached (2 sheets).

D. C. Quenelle et al.; "Treatment of Tuberculosis Using a Combination of Sustained-Release Rifampin-Loaded Microspheres and Oral Dosing with Isoniazid;" Antimicrobial Agents and Chemotherapy, vol. 45, No. 6, Jun. 2001, pp. 1637-1644.

Gursel et al., Models of Astrocytoma, Drug Discovery Today, Disease Models, 2005, 2, 77-83.

Contreras et al., HIV Latency: Present Knowledge and Future Directions, 2006, 1(6), 733-745.

H. Murakami et al., "Utilization of poly(DL-lactide-co-glycolide) nanoparticles for preparation of mini-depot tablets by direct compression," Journal of Controlled Release, vol. 67, Issue 1, Jun. 15, 2000, pp. 29-36.

Communication pursuant to Article 94(c) EPC dated Jul. 27, 2012, issued for the European Patent Application No. 03791347.2.

* cited by examiner

FINE PARTICLE PHAGOCYTIC MACROPHAGES

DRUG INCLUSION FINE PARTICLES

DRUG   MACROPHAGES

MEDICAL SOLUTION SOAKING MACROPHAGES

MEDICAL SOLUTION

DRUG   MACROPHAGES

DRUG CONCENTRATION IN THE FINE PAETICLE

DRUG

MACROPHAGES

≫

DRUG

MACROPHAGES

F I G. 5
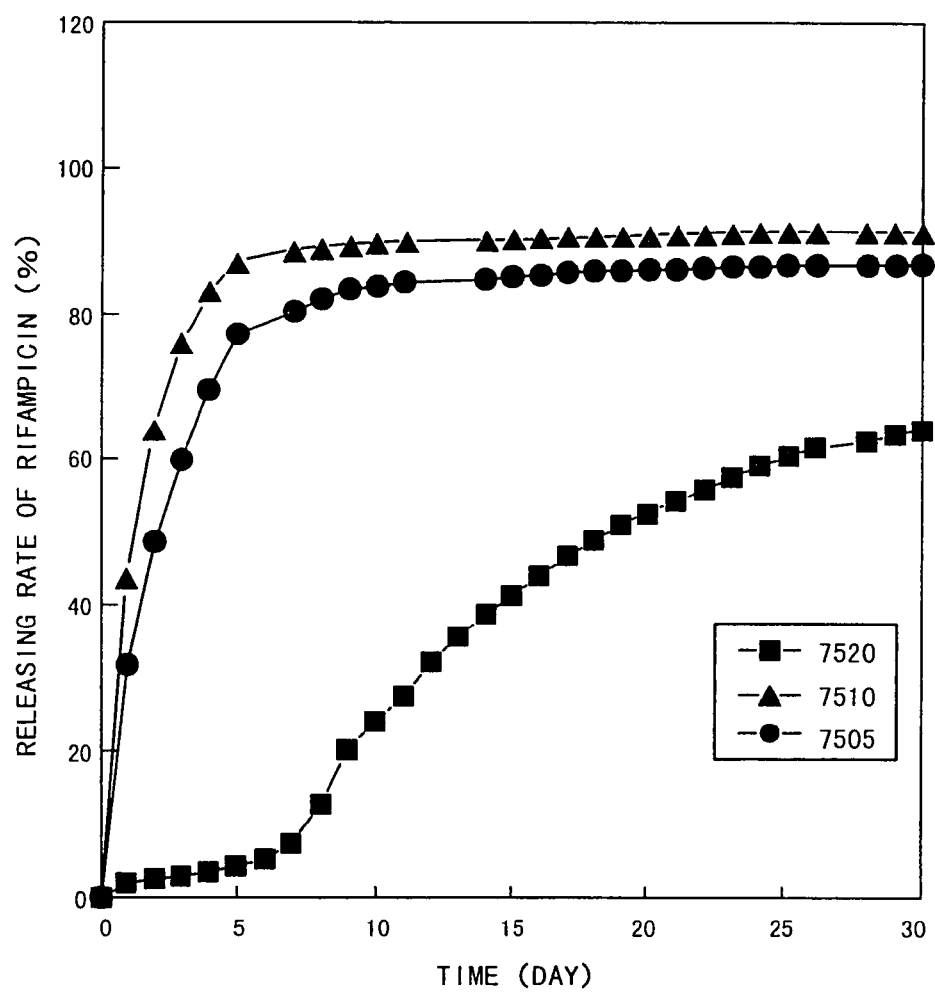

F I G. 7
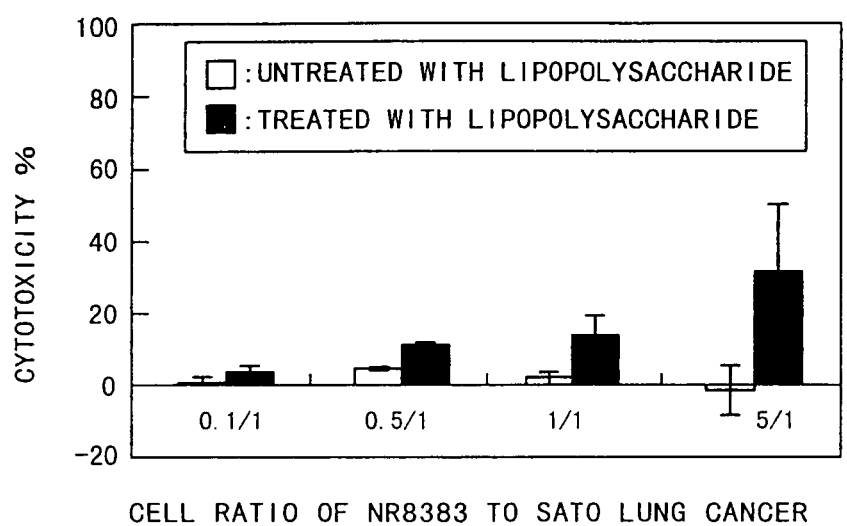

REMEDY

This application is a divisional application of U.S. application Ser. No. 10/525,964, filed Oct. 13, 2005, and claims the right of priority under 35 U.S.C. §119 based on Japanese Patent Application No. 2002-247871 filed Aug. 27, 2002, which is hereby incorporated by reference herein in its entirety as if fully set forth herein.

TECHNICAL FIELD

The present invention relates to a remedy to normalize macrophages with dysfunction by taking advantage of the phagocytic capacity of macrophages, or effective for various infectious pathogens. The remedy according to the invention is aimed at all substances given on a therapeutic and/or diagnostic basis and assemblies thereof, and a formulation thereof is a medical mixture of a medicament (including a medicament carrier in some cases) and the medicament carrier.

BACKGROUND ART

I. Macrophage

First, a macrophage which plays a central function in an action of a remedy according to the invention is reviewed.

Morphology and functions of the macrophage are described in detail, for example, in "Seimei o sasaeru Macrophage (Macrophage Which Supports Life)" authored by Kiyoshi Takahashi (Bunkodo, 2001), and the background related to the invention is as follows. The macrophage is a cell which configures a mononuclear phagocyte system (MPS). A monocyte in blood is derived from a hematopoietic stem cell in bone marrow, divides/differentiates in the bone marrow to flow out into the blood, and settles in various tissues to differentiate a monocytic cell called by various names. This cell is referred to as a histiocyte in connective tissue, Kupper cell in the liver, an alveolar macrophage in the lung, a macrophage in the lymph node and spleen, a thoracic macrophage/peritoneal macrophage in a body cavity, an osteoclast in bone, Langerhans cell in skin, a microglia cell in nerve tissue, a microglia in the brain, and an A type cell in synovial membrane, and has tissue-specific natures.

1. General Characteristics (1) It is a mononuclear cell with a diameter of about 15 to 20 μm, is abundant in cytoplasm, and easily adheres to a surface of glass and plastic. It moves with pseudopodia and has a strong phagocytosis of foreign substances.

(2) It is a host defense cell.

(3) It has a foreign substance-eliminating capacity and an immunological competence.

(4) It presents antigen information to a T lymphocyte to establish immunity.

(5) It is activated by interferon to become an effector in cell mediated immunity.

(6) It is more resistant to X-rays than a lymphocyte.

2. Physiological Significance of Macrophage (1) Phagocytic Capacity

Phagocytosis is one of the best-known functions of the macrophage. This function may be believed to be one of the most basic functions which has been comprised since organisms were single-cell organisms in the process of evolution from the beginning of life. Therefore, one of features of the macrophage is that its existence has universality species-transversely. It seems that this feature provides one of the great advantages for research on macrophage functions. That is, if a remedy for diseases of mammals is developed/researched, macrophages from other than mammals can be functionally useful as research material. This is due to an aspect that the macrophage is a phylogenetically conserved cell.

(2) Host Defense Function

A second important aspect as the macrophage functions is a host defense action. This action is referred to as a non-specific host defense action, but recent research has demonstrated that the host defense action of the macrophage is also specific. Originally, the term, non-specificity has been a word corresponding to antigen specificity and immunological memory characterized for the T cell, and at present, it has not been proved that the macrophage has the antigen specificity or the immunological memory in an accurate sense. Thus, it is not exactly wrong that the host defense action of the macrophage is non-specific. However, for example, the response of macrophages is qualitatively different depending on types of pathogens, and a part of these qualitatively different responses correspond to a difference in receptors on a macrophage cell surface, which recognizes the pathogens. Thus, viewed from the side of cellular response to stimulation of a foreign substance (environment), it can be said that the action of macrophages is specific.

Nowadays, it becomes common to understand the host defense action based on the macrophages as an innate immune system and the host defense action based on the T cells as an acquired immune system. Furthermore, considering the phylogenetic universality, it is a matter of course that the innate immune system is also a phylogenetically highly conserved host defense system.

(3) Innate Immune System

The innate immune system based on the macrophages plays a central role in the host defense system which are the foreign substance discrimination and elimination system in not only species not having the acquired immune system but also species comprising the acquired immune system. Even in organisms comprising the acquired immune system, the function of the innate immune system covers the discrimination and elimination of foreign substances in nearly all cases, and in the case where this is insufficient, the acquired immune system is recruited. Even in this case, the antigen presentation by the macrophage is essential for the specific recognition of the foreign substance, and when eliminating the foreign substance, those which play central roles in the elimination system are the macrophages and the like which are the cells which configure the innate immune system.

(4) Elimination of Foreign Substances

On the other hand, endogenous foreign substances are eliminated by cytotoxic T cells characteristic of the acquired immune system (e.g., elimination of cells infected with virus), but other T cells presented with the antigen by the macrophages are essential for proliferation and maturation of these cytotoxic T cells. That is, in order for the acquired immune system to significantly serve, the innate immune system must serve completely and suitably to the end.

(5) Failure of Function

Therefore, failure of function of the phagocytosis or the antigen presentation of the macrophages can primarily become a potential cause of immunodeficiency. To put it concretely, the followings are known as the failure of function and diseases related to the aspects set forth in the above I.1 (General characteristics of macrophages). That is:

1) Leukocyte adhesion deficiency, Chediac-Higashi syndrome and the like are known as a phagocytic function abnormality as an abnormality of foreign substance phagocytosis. In both cases, the abnormality is observed in the phagocytic function, and in the latter, transport of a lysosomal enzyme to a phagocytic void cavity is abnormal, thus the disinfection capacity is reduced and the phagocytic capacity is remarkably facilitated.

2) As the disease as the abnormality of the host defense, chronic mucocutaneous candidiasis is included. In the macrophages in a patient with this disease, the migration capacity is reduced and disinfection capacity of candida is also reduced.

3) As the disease as the abnormality of the foreign substance elimination capacity and the immunological competence, Wiskott-Aldrich syndrome can be included. The macrophages of the patient exhibit a complicated immunological abnormality such as migration abnormality and defect of an antibody dependent cytotoxic action.

4) As the dysfunction for presentation capacity of antigen information, major histocompatibility complex (MHC) class II antigen deficiency where severe immunodeficiency is caused regardless of normal T and B cells is known.

5) As the dysfunction in the aspect that the macrophage is activated by an interferon to become the effector of the cell mediated immunity, interferon receptor deficiency where a child with a deficient interferon receptor cannot defend tubercular infection, which becomes fatal is known.

Furthermore, a mammal with deficiency of the acquired immune system can exist and live, but the animal with deficiency of the macrophage cannot exist. And, it is being demonstrated that physiologically active substances collectively referred to as cytokines which perform intercellular signaling play important roles in the host defense system based on the discrimination and elimination of a foreign substance. The macrophages produce and secrete a wide variety of cytokines. In this way, the macrophage functions are essential for individual homeostasis also with respect to the discrimination and elimination of a foreign substance.

(6) Anatomical Features

Anatomical features of the macrophage are different depending on tissue-specific macrophages which are resident in various tissues and have inherent characters. This is obvious when observed in the mucosal tissue which is a point of contact between an individual and an environment. Specific macrophages are resident in submucous layers of the respiratory organ, digestive organ and genitourinary organ, respectively. These tissue-specific macrophages biologically respond to tissue-specific internal and external environments. This suggests that the macrophages play an important role for organism homeostasis in addition to the discrimination and elimination of a foreign substance. There are many unknown aspects in the physiological significance of the tissue-specific macrophages. On reflection, considering an existence significant of the tissue-specific macrophages from a new viewpoint, their relation to various pathologies may be now brought to attention.

(7) Relation to Pathology

Because if we think of the physiological significance that the macrophage plays a central role in the immune system, it is strongly suggested that the dysfunction of the tissue-specific macrophage is involved in the induction of tissue-specific pathologies. In fact, in many intractable diseases such as Crohn's disease which is one of the inflammatory intestinal diseases, further autoimmune disease such as rheumatoid, and aging diseases such as osteoporosis, the dysfunction of the macrophages is involved in some form. In chronic infections of acid-fast bacteria such as tuberculosis germs, in addition to problems of the acid-fast bacteria per se, it may be thought that the dysfunction of the alveolar macrophages is present in the context of the pathology. Considering in this way, it can be said that development of a remedy which increases the phagocytic capacity of the macrophage as a target cell and consequently increases a concentration of the remedy in the macrophage is an extremely important and reasonable subject for providing a novel therapy of intractable diseases including infectious diseases such as tuberculosis for which there is currently no effective therapy.

II. Dysfunction of Macrophages and Diseases (1) Macrophage as Infectious Pathogen Vehicle According to WHO, tuberculosis, AIDS, malaria and the like are chronic intractable diseases which must be considered to be the most important on a worldwide scale. For example, it is described that 800 million or more patients with tuberculosis occur annually and 300 million die. It is an urgent task to develop a remedy (medicament/formulation) effective in response to these diseases, and its social significance is extremely great.

On the other hand, with respect to infection defense of and elimination of a pathogen, one of the cells which plays the most important role in vivo is the macrophage. In fact, the macrophages are distributed in all organs. These macrophages are different in morphology and functions depending on the organs where the macrophages exist, but they are common in the aspect that they perform the infection defense/elimination of the pathogen.

On the other hand, infectious pathogens have acquired various means for avoiding attack from the macrophages in the process of evolution. Furthermore, the infectious pathogens are often hidden in the macrophages to make the macrophage a host. It is a matter of course that the pathogen which has succeeded to parasitize in the macrophage in this way causes an infectious disease chronically and repeatedly, and it is not unusual to result in a fatal consequence. That is, in this case, the macrophage which should primarily accomplish the infection defense/elimination of a pathogen serves as an infectious pathogen vehicle in reverse.

(2) Pathogens in Macrophages

A typical example thereof can be observed in tuberculosis. That is, the pathogen (*Mycobacterium tuberculosis* or *Mycobacterium bovis*) is phagocytosed by the macrophage in the pulmonary alveolus which is an infectious pathway in an early stage, and is stably present in a phagosome formed at that time. That is, the pathogen can live by making the macrophage which should primarily digest it as a "shelter". In addition, many causative pathogens such as *Mycobacterium leprae* which is a causative pathogen of lepra, *Mycobacterium avium* which is a causative pathogen of atypical mycobacteriosis, *Chlamydia pneumoniae, Chlamydia trachomatis* or *Chlamydia psittaci* which is a causative pathogen of chlamydiosis of the intractable diseases whose radical therapy has not been established and propagation has been feared are common in the aspect that the macrophage becomes the infectious pathogen vehicle.

For tuberculosis germs, AIDS virus and the like, numerous efforts are given for their prevention. However, once the infection is established, there is no effective therapy. Even if a compound having a direct disinfection action against the infectious pathogen is present, in general it is not easy to accomplish a concentration in the macrophage with the pathogen, which is sufficient to exterminate the specific pathogen (exterminating in the invention means that all or a part of the pathogens are exterminated to vanish.) by simply administering an appropriate remedy.

DISCLOSURE OF THE INVENTION

Accordingly, even if extracellular pathogens can be exterminated by administering an effective remedy, the macrophages as the pathogen vehicles are still alive as pathogen sources and continue to supply the pathogens. The above is a reason why currently there is no radical therapy for the pathogen which parasitizes in the macrophage. The invention makes this point a subject. Conversely, if it is possible to exterminate the macrophages infected with the pathogens as the pathogen vehicles or exterminate the pathogens in the macrophages infected with the pathogens, many chronic intractable infectious diseases described above can be radically treated. Therefore, it is an object of the invention to provide a remedy for a disease caused based on dysfunction of the macrophage or by making a macrophage a vehicle.

As a result of an intensive study, the present inventors have led to a remarkably novel idea where it is an object to exterminate macrophages infected with pathogens as pathogen vehicles, exterminate the pathogens in the macrophages infected with the pathogens and act upon macrophages whose function has become abnormal due to a disease, and have completed the invention.

A remedy of the invention is characterized by facilitating a phagocytic activity of macrophages and exterminating pathogens in the macrophages.

Also, the remedy of the invention is characterized by facilitating the phagocytic activity of macrophages and leading the macrophages to cell death.

Also, the remedy of the invention is characterized by facilitating the phagocytic activity of macrophages and acting upon macrophages in a dysfunctional state.

Also, it is desirable that the remedy of the invention is for any of mycobacteriosis, AIDS, chlamydiosis or toxoplasmosis. This enables to effectively treat the diseases where the macrophages retain the pathogens.

Also, it is desirable that the remedy of the invention is for Crohn's disease, rheumatoid, cancer or immunodeficiency syndrome. This enables to effectively treat the diseases where the macrophages are in a dysfunctional state. AIDS is included in the immunodeficiency syndrome.

Also, it is desirable that the above macrophages are those which are resident in mucosal tissues. This enables to effectively treat the disease at sites such as the respiratory organ, digestive organ and genitourinary organ where the pathogens cause primary infection.

Also, it is desirable that the above macrophages are those which are resident in any of the peritoneal cavity, greater omentum, milky spot, pulmonary alveolus, pulmonary stroma, liver, portal vein area, spleen, bone marrow, thymus, digestive tract, palatine tonsil, adrenal gland, pituitary, thyroid stroma, Langerhans islet, parathyroid gland, pineal gland, testis, ovary, oviduct, uterus, placenta, skin, meningis, brain substance and choroid plexus, or that the above macrophages are microglia, precursor cells of microglia, glia cells, precursor cells of glia cells, precursor cells of the above resident macrophages, analogous cells of the above resident macrophages, or precursor cells of the above resident macrophage analogous cells. This enables to effectively treat the diseases caused in various organs and tissues in the body.

Also, the remedy of the invention is characterized by containing PLGA [poly(lactic acid/glycolic acid)copolymer] and being in response to the tuberculosis.

Also, it is desirable to contain rifampicin. This enables to provide the remedy to exterminate tuberculosis germs.

Also, it is desirable to contain PLGA with a molecular weight of 1,500 to 150,000. This enables to provide a fine particle formulation which is biodegradable and is phagocytosed by the macrophages.

Also, it is desirable to contain PLGA with a molecular weight of 1,500 to 75,000. This enables to provide a fine particle formulation which is phagocytosed by the macrophages and easily releases a medicament in the macrophages.

Also, it is desirable to further contain at least one of PVA (polyvinyl alcohol), PEG (polyethyleneglycol), PEO (polyethylene oxide), sugar, protein, peptide, phospholipid, or cholesterol. This enables to provide a fine particle formulation which is actively phagocytosed depending on types of the macrophages.

Also, it is desirable to further contain at least one of PVA, PEG, PEO, sugar, protein, peptide, phospholipid, or cholesterol and to be a fine particle formulation where major particle diameters are 1 to 6 µm. This enables to effectively take advantage of a phagocytic function of the macrophage to incorporate in the macrophages.

Also it is desirable to facilitate the phagocytic activity by being phagocytosed.

The present specification includes contents described in the specification and/or the drawings of Japanese Patent Application No. 2002-247871 which is the basis of priority of the present application.

BRIEF DESCRIPTION OF THE DRAWINGS

FIG. 5 is a view (No. 2) illustrating a rifampicin-retaining capacity of RFP-PLGA fine particles, i.e., that amounts of rifampicin released are different depending on compositions of PLGA fine particles. Experimental values contain an uncertainty of 5%.

FIG. 7 is a view illustrating that a cytotoxic effect of alveolar macrophages NR8383 in a dysfunctional state by co-culture with Sato lung cancer cells on the Sato lung cancer cells is enhanced by activating a phagocytic capacity of NR8383 using lipopolysaccharide. Open squares indicate the cytotoxic effect of NR8383 without treatment with lipopolysaccharide on the Sato lung cancer cells, and solid squares indicate the cytotoxic effect of NR8383 treated with lipopolysaccharide (1 µg/mL) on the Sato lung cancer cells (co-cultured for 4 hours). The cytotoxic effect (%) was evaluated by calculating amounts of lactate dehydrogenase released in media.

BEST MODE FOR CARRYING OUT THE INVENTION

Figure 1:
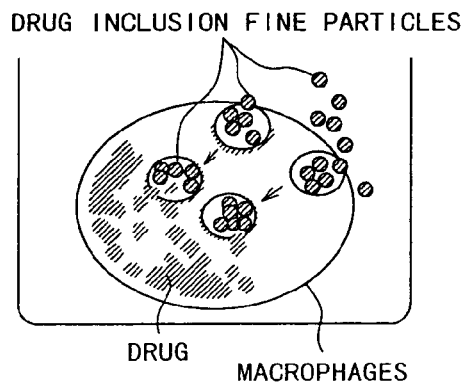
FIG. 1 is a view illustrating by comparison a drug concentration in a macrophage of a remedy of the invention with that of a conventional remedy.
Figure 1:
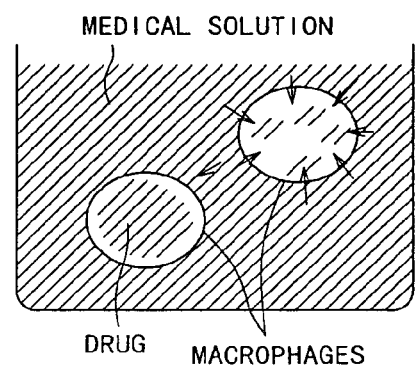
Figure 1:
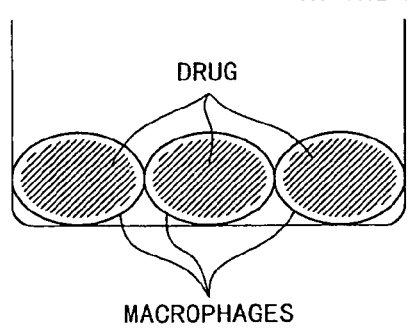
Figure 1:
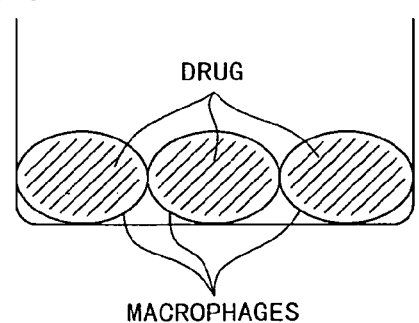

Hereinafter, suitable embodiment modes of the invention are described in detail in reference to the accompanying drawings. However, the technical scope of the invention is not limited by these embodiment modes.

One of the functions comprised in whole macrophages and specific for the macrophages includes phagocytosis. The phagocytosis is a function in which a solid with a size of about 1 μm or more is actively incorporated in a macrophage cell.

On the other hand, if a solid made artificially is actively phagocytosed, it is possible to accumulate the solid in the macrophage at a concentration which cannot be usually accomplished. Such a solid can be generally provided as a particle, but to actively phagocytose, it is necessary to optimize a particle diameter, particle surface property (having a charge, having a certain flexible structure, etc.) advantageous for phagocytosis. For example, it is possible to prepare the particle which is easily phagocytosed by the macrophage using a material where polylactate and polyethyleneglycol are mixed as a substrate.

Thus, if a medicament which acts upon infectious pathogens or macrophage infected with the pathogens is blended to prepare the particle, along with phagocytosis of the particle, the medicament is also actively incorporated in the macrophage.

An essential part of the invention is in the aspect that diseases due to dysfunction of the macrophage (I. 2. (5), (7), II. (1), mycobacteriosis, AIDS, chlamydiosis, toxoplasmosis, cancer and the like) are treated by taking advantage of the phagocytic function that the macrophages have. Thus, the above object is accomplished by preparing a formulation in which a medicament effective for them is contained in fine particles (medicament carrier) which can be phagocytosed by the macrophages.

Typically, for the formulation which is a medical mixture of the medicament carrier and the medicament, it is necessary to design in order to avoid the phagocytosis by macrophages. However, the invention has a novelty in the aspect of actively taking advantage of phagocytic activity of the macrophage based on an idea which completely reverses the conventional beliefs.

As aforementioned, as one of the host defense functions of macrophages, there is the phagocytosis. The phagocytosis is an inherent function characteristically observed in the macrophages, and it is possible to incorporate particles with a size which cannot be incorporated by cells other than the macrophages. Pathological microorganisms such as bacteria are phagocytosed by the macrophages and decomposed in the macrophages. Therefore, one of biological significance of the phagocytic function of the macrophages is to impair the pathological microorganisms. Moreover, the macrophages are activated by the phagocytosis and become able to oppose pathological microorganisms in some cases. This is a phenomenon known as macrophage activation by phagocytosis, and this enables the macrophages to damage even cancer cells. Therefore, if the macrophages can be activated by the phagocytosis to enhance the phagocytic activity, it becomes possible to exterminate the pathological microorganisms more intensively.

In order for particles to be phagocytosed, it is believed that it is necessary to comprise the following natures (phagocytosable property)

That is:

A particle diameter is 1 to 6 μm. Such a particle is referred to as a fine particle.

A particle surface is wetted with a medium (body fluid around the macrophages in vivo) of macrophages, but the particle is not immediately dissolved and is present as the particle for a certain time period.

The particle is a solid in a temperature range of 20 to 45° C.

A specific gravity of the particle is larger than that of the medium (body fluid around the macrophages in vivo) of macrophages.

The particle has a surface layer through which water and ions are permeable.

On the other hand, considering that the particle is administered in vivo, the particle surface is required to have a macromolecular layer with high histocompatibility. It is necessary to retain a particle form until being incorporated in the macrophage while being metabolized by decomposing into components non-toxic for the body in vivo (degradability in vivo) after being incorporated in the macrophage or when not being incorporated.

As a macromolecule which fulfills the above two conditions and can be easily molded into a particle, poly(lactic acid/glycolic acid)copolymer (hereinafter referred to as "PLGA") or polylactic acid (hereinafter referred to as "PL") is a candidate. PL is more hydrophobic and requires a longer time until being decomposed than PLGA. On the other hand, PLGA changes the decomposing rate depending on the monomer ratio. The larger the molecular weight is, the longer time it takes until being decomposed. When the molecular weight of PLGA is 1,000 or less, there is a possibility that it is present as a liquid in the temperature range of 20 to 45° C. Therefore, the molecular weight of PLGA which is present as a solid in the temperature range of 20 to 45° C. is desirably 1,500 or more.

Furthermore, for the release of a medicament contained in the PLGA particle from the particle, in the case of PLGA with a molecular weight of about 20,000, the medicament is released in an almost zero order. That is, a released amount is always retained constantly. However, in the case of the PLGA particle with a molecular weight of about 44,000 or 75,000, a pulse type release where the medicament is released after a constant time period rather than the zero order release has been observed. Moreover, the time period where the pulse type of a medicament release is observed is delayed in the PLGA formulation with a large molecular weight. That is, a pattern of the medicament release from the PLGA particles depends on the molecular weight of PLGA. Additionally, it is predicted that the decomposing rate of PLGA related to the medicament release is not only delayed along with molecular weight increase of PLGA, but also the rate is faster in vivo such as in the macrophage than in vitro, and thus it appears that it is possible to effectively use those having a range of molecular weight up to 150,000.

From the above points of view, it appears that a fine particle formulation with particle diameters of 1 to 6 μm made up of PLGA where a molecular weight is 1,500 to 150,000 and a monomer ratio of lactic acid/glycolic acid is 50:50 to 75:25 (acceptable range) and a fine particle formulation with particle diameters of 1 to 6 μm made up of PLGA where a molecular weight is 5,000 to 75,000 and a monomer ratio of lactic acid/glycolic acid is 50:50 to 75:25 (suitable range) are easily phagocytosed by the macrophages and are optimal for the object that the medicament is released while holding a constant persistence from the fine particle formulation which internally includes the medicament in the macrophages.

Provision of Novel Remedy which Enables Specific Extermination of Macrophages which Retain Infectious Pathogens By actively taking advantage of specific phagocytic activity of the macrophages which retain various infectious pathogens including tuberculosis germs, in order to exterminate the pathogens in the macrophages or the macrophages per se retaining the pathogens, the following remedies are effective.

(1) A remedy which facilitates the phagocytic activity of the macrophages.

(2) A remedy having a direct exterminating effect on the infectious pathogens in the macrophages.

(3) A remedy which acts upon the macrophages.

For the remedy of (1), those having the nature which fulfills the aforementioned two conditions (phagocytosable property and in vivo degradability) are adequate, but preferably, it is desirable to have the nature capable of being phagocytosed selectively by the macrophages which retain/do not retain the infectious pathogens. Conventionally, it has been known that a substance which activates the phagocytic activity of the macrophages is present (matter known in the art). An attempt to develop a remedy which acts upon the pathogens in the macrophages by actively taking advantage of this nature is not performed at all (novel matter). In the types of (2) and (3), not only various medicaments which directly act upon the pathogens are intended but also genes per se such as DNA or RNA having an action to modify physiological functions of the macrophages which retain/do not retain the pathogens can be used as the medicaments. An attempt to develop a remedy effective for eliminating the infectious pathogens by combining (1), (2) and (3) has not been carried out at all, and the remedy of the invention is a new type remedy effective for the treatment of infectious pathogens (novel matter).

Figure 4:
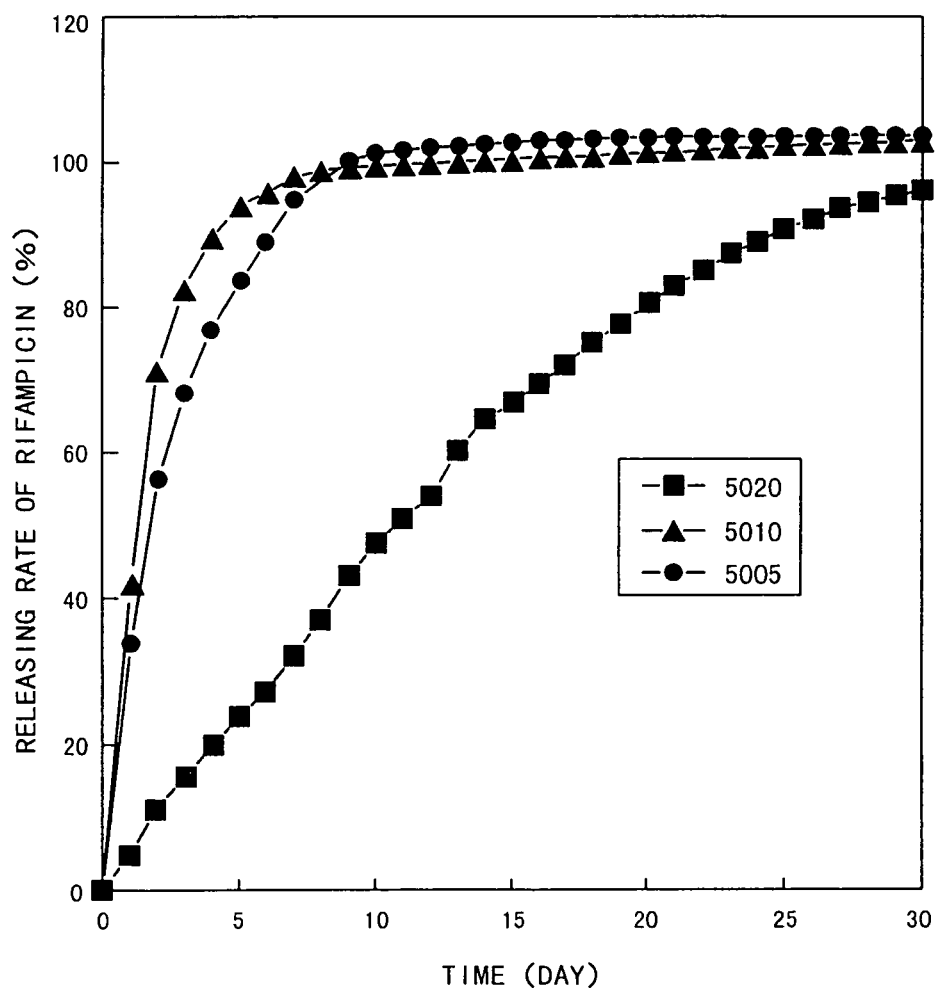
FIG. 4 is a view (No. 1) illustrating a rifampicin-retaining capacity of RFP-PLGA fine particles, i.e., that amounts of rifampicin released are different depending on compositions of PLGA fine particles. Experimental values contain an uncertainty of 5%.

For example, in Antimicrobial Agents and Chemotherapy (Vol. 42, No. 10:2682-2689, 1998), an antituberculous action of particles containing rifampicin in PLGA is disclosed. However, in this report, facilitation of the phagocytic activity by PLGA particles is not described at all. Furthermore, since in the PLGA particles containing rifampicin, drug efficacy as an antituberculous drug is not enhanced compared to rifampicin alone, it is evident to have different characteristics from those of the particles of the invention. Furthermore, as shown in FIG. 4 and FIG. 5, the molecular weight of PLGA is important for controlling the release of rifampicin. However, in the above report, the molecular weight of PLGA used during the preparation of PLGA is not described. It is presumed that probably because of using PLGA having a different molecular weight from that of the particles of the invention, it did not lead to having the function of an antituberculous drug. When preparing the PLGA particles having the antituberculous drug activity, using those which are proper with respect to the molecular weight of PLGA, the monomer ratio and the diameters of the prepared particles, the incorporation of the particles by phagocytosis of the macrophages and the antituberculous activity in the macrophages must be evaluated. Taken together the above aspects, in the PLGA particles described above, a certain commonality for the materials is observed because the monomer ratio of PLGA and the diameters of particles fall in the "suitable range" of the invention, but correct characteristics for the particles are not described and the antituberculous drug action is not observed. Therefore, it is difficult to reach a prior example which denies novelty and the inventive step of the invention.

Furthermore, in Pharmaceutical Research (Vol. 17, No. 8:955-961, 2000), a method for preparing particles containing rifampicin made using PLGA with a molecular weight of 82,500 is disclosed. This method for preparing the particles is different from that of the invention. A tuberculosis germ-exterminating effect of rifampicin-containing PLGA particles using PLGA with a molecular weight of 82,500 is disclosed in Pharmaceutical Research (Vol. 18, No. 9:1315-1319, 2001). This shows that the antituberculous activity of the rifampicin-containing PLGA particles is inferior to the effect of rifampicin alone in vitro and that it cannot be said that there is an obvious treatment effect in animal experiments. In order for the rifampicin-containing PLGA particles to elicit the antituberculous action, the particles must have appropriate degradability and a high rate of internally included rifampicin. However, in the aforementioned article, such characteristics for which the activity depends have not been examined, and the antituberculous activity has been investigated. It is known that the degradability and the internally included rate are reduced in the PLGA particles with large molecular weight, and thus, it appears that because of the use of PLGA with high molecular weight of 82,500, the antituberculous action was not elicited. As in the above, similar research to those presented in the invention have been performed, but the attempt to exterminate the intracellular parasitic pathogens through intending to take advantage of the phagocytic activity of the macrophage and accomplishing this activation has never been performed. Also, the rifampicin-containing PLGA has been prepared, but no proper research for preparation methods and material property for the purpose of enabling to accomplish the object of the invention has been performed. Additionally, in Pharmaceutical Research (Vol. 18, No. 10:1405-1410, 2001), there is a description that it is supposed that the rifampicin-containing PLGA particles are incorporated in the macrophages. However, also in this case, the particles have not been actively incorporated by the macrophages, or no formulation where the activation is intended has been made, and in fact, no phagocytic rate of the rifampicin-containing PLGA particles has been examined. Incidentally, the concentration of rifampicin in the macrophages in vitro using the rifampicin-containing PLGA particles described in this report is only 0.45 µg/$10^6$ cells. In the case of using the rifampicin-containing PLGA fine particles, not only is the phagocytosis activated but also the concentration of rifampicin in the macrophages reaches 6 µg/$10^6$ cells which is 13 times or more. From the above, if intending to induce the phagocytosis in the macrophages and exterminate the pathological microorganisms in the macrophages, it is evident that it is difficult to accomplish this only by containing the drug in microspheres. Furthermore, in any previous reports, it has not been examined whether the rifampicin-containing PLGA particles exterminate intracellular tuberculosis germs using the alveolar macrophages which are the target cells of the tuberculosis germs. As is evident in reference to the aforementioned "Macrophage Which Supports Life," the macrophages are highly tissue-specific, and thus it is a well-known fact that the result obtained using the macrophages present in blood cannot apply to the tissue-specific macrophages, e.g., the alveolar macrophages. That is, as a novelty of the invention, the novelty of the concept is a matter of course. Examples which support this concept include the aspects that the alveolar macrophages are used and the phagocytic activity of the cells is induced, and the high medicament concentration is actually retained in the alveolar macrophages, and the rifampicin-containing PLGA particles are produced and provided where the extermination of tuberculosis germs in the alveolar macrophages by the formulation is obviously more excellent than that by rifampicin alone.

On the other hand, it has been widely known that production of non-specific antibacterial substances, e.g., hydrogen peroxide and oxygen radical from the macrophages is enhanced by the phagocytosis of the particles by the macrophages. For example, in the European Journal of Pharmaceutical Sciences (Vol. 15, pp. 197-207, 2000), it is disclosed that the production of hydrogen peroxide from cultured macrophages whose characters resemble those of monocytes in blood is enhanced by phagocytosing PLGA particles. However, it is not described that the phagocytosis of PLGA by the macrophages enhances the phagocytic activity. Furthermore, since the activation of macrophages is extremely diverse, the enhancement of hydrogen peroxide production by the phagocytosis is not directly combined with enhancement of the phagocytosis.

When actual treatment of the infectious disease is performed, a formulation in which a medicament of type (2) or (3) is contained in a remedy of type (1) is effective. That is, in order for the remedy of type (2) or (3) to effectively act in the macrophages, the remedy of type (1) facilitates the phagocytic activity of the macrophages to enhance the function which carries the remedy of type (2) or (3) into the macrophages. That is, as shown in FIG. 1, the remedy intended by the invention is easily phagocytosed by the macrophages, facilitates the phagocytic activity by being phagocytosed, and thus the concentration of the remedy in the macrophages becomes remarkably higher compared to the case of administering the remedy alone. That is, in comparison to the drug incorporated into the macrophages in a conventional drug solution on the right side, internal drug-including fine particles according to the invention on the left side are actively incorporated into the macrophages to increase the drug concentration in the macrophages. In this way, "facilitating the phagocytic activity of the macrophages" described in the Claims mean that the concentration of the remedy in the macrophages becomes remarkably higher compared to the case of administering the remedy alone because the remedy enhances the phagocytic capacity of the macrophages.

Specific Application Example

Tuberculosis

Tuberculosis is set forth as one example with respect to the effectiveness of the remedy presented in the invention. Tuberculosis germs invade from the respiratory tract to pulmonary alveoli by droplet, and are phagocytosed by alveolar macrophages. Typically, phagocytosed pathogens are destined to be decomposed by an attack of protease in cells. However, the tuberculosis germs avoid the attack of protease and are alive in the macrophages. These tuberculosis germs in the macrophages migrate out of the macrophages, and persistently supply the tuberculosis germs in a host body. At present, as antituberculous drugs, medicaments such as isoniazid, rifampicin, streptomycin sulfate and ethambutol are used. All medicaments are effective for the tuberculosis germs out of the macrophages, but do not exhibit any effect on the tuberculosis germs in the alveolar macrophages. This is mainly attributed to that a medicament concentration sufficient to exterminate the tuberculosis germs is not obtained in the alveolar macrophages.

Thus, if the medicament concentration sufficient to exterminate the tuberculosis germs is obtained in the alveolar macrophages by taking advantage of the phagocytosis of the alveolar macrophages, it is also possible to exterminate the tuberculosis germs in the alveolar macrophages. In this case, the phagocytosis is utilized in order to selectively increase the medicament concentration in the macrophages.

A. Remedy which Enhances Phagocytic Capacity of Macrophages

Using PLGA as an example, a method for producing a remedy which enhances the phagocytic capacity of macrophages and effects thereof are described.

I. Enhancement of Phagocytic Capacity of Macrophages by PLGA Fine Particle Formulation (in this Section, a PLGA Fine Particle Per Se is a Medicinal Ingredient.)

1. Method for Preparing PLGA Fine Particles (a) Materials (1) PLGA [poly(lactic acid/glycolic acid)copolymer], monomer ratio: 75:25, molecular weight: 20,000 (Wako Pure Chemical Industries Ltd., PLGA-7520)

(2) PVA (polyvinyl alcohol) polymerization degree: 500

(b) Preparation of PLGA Fine Particle Formulation (1) 500 mg of PLGA is dissolved in 1.5 mL of methylene chloride.

(2) PVA is dissolved in water to become 0.3% (w/v).

(3) When 8 mL of a PVA aqueous solution of (2) is added to a solution of (1) and stirred for 3 minutes, an oil-in-water (o/w type) emulsion is formed.

(4) (3) is added into 200 mL of a PVA aqueous solution of (2), and stirred at room temperature at 520 rpm for 3 hours.

(5) A fine particle formulation is precipitated by centrifugation (3,000 rpm, 15 minutes), separated, and further washed twice by adding 10 mL of distilled water using a centrifuge.

(6) Drying under reduced pressure in a desiccator for 24 hours.

Figure 2:
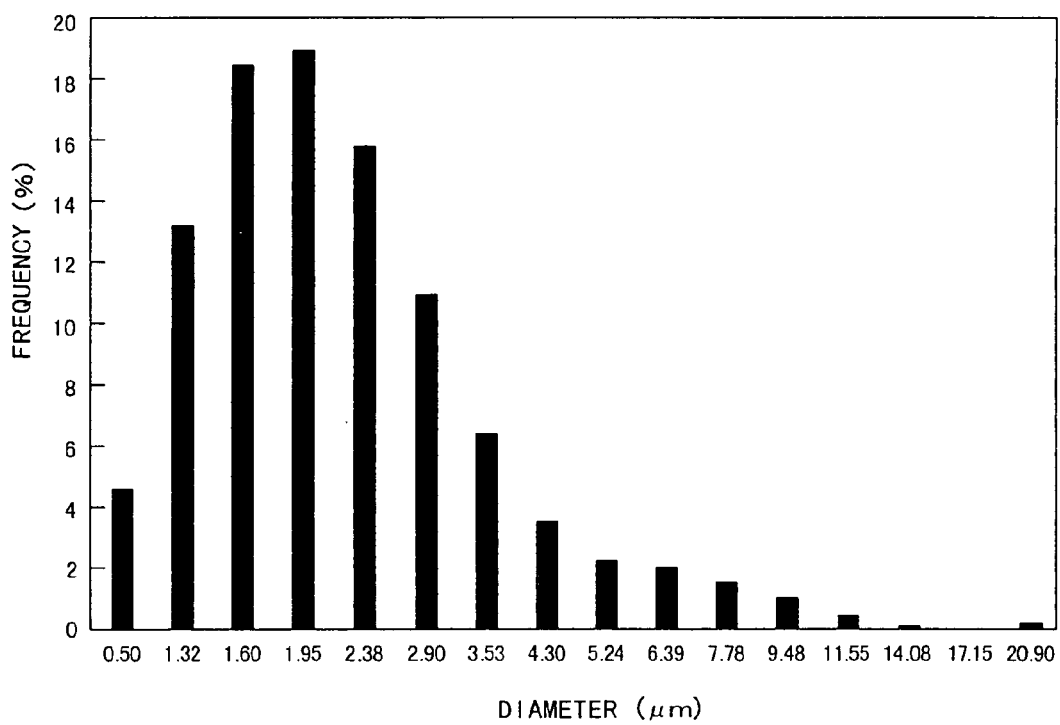
FIG. 2 is a view showing a particle diameter distribution of a fine particle formulation in an embodiment mode of the invention.

(7) A particle diameter distribution of the resulting fine particle formulation is shown in FIG. 2. As is evident from this figure, the prepared fine particle formulation has a peak at a diameter of about 2 µM and has a distribution between 1 to 10 µm. This particle is a solid at ambient temperatures. A yield calculated from PLGA (500 mg) used for the preparation and an entire weight of the recovered formulation was about 90%.

(8) Other examples

Characteristics (molecular weight and composition) of the PLGA fine particles additionally made are correctively shown below.

1. PLGA-5005 (PLGA, molecular weight: 5,000; lactic acid/glycolic acid: 50:50)

2. PLGA-5010 (PLGA, molecular weight: 10,000; lactic acid/glycolic acid: 50:50)

3. PLGA-5020 (PLGA, molecular weight: 20,000; lactic acid/glycolic acid: 50:50)

4. PLGA-7505 (PLGA, molecular weight: 5,000; lactic acid/glycolic acid: 75:25)

5. PLGA-7510 (PLGA, molecular weight: 10,000; lactic acid/glycolic acid: 75:25)

The method for preparing the PLGA fine particle formulation is the same as 1. (b)(1) to (6) except the kind of PLGA.

An average particle diameter of the resulting fine particle formulation was about 2 µm even when any PLGA was used. A yield calculated from PLGA (500 mg) used for the preparation and an entire weight of the recovered formulation was about 90%.

2. Enhancement Effect on Phagocytosis of Alveolar Macrophages by Phagocytosing PLGA Fine Particle Formation (1) Alveolar macrophage cells (NR8383 cells) are prepared at $1 \times 10^6$ cells/mL in a medium (Ham F-12K, 15% fetal calf serum), added in a 24-well plate, and 0.04, 0.4 or 4 µg of PLGA-7520 fine particle formulation is added thereto, which is then cultured in a carbon dioxide gas incubator (37° C.).

(2) One hour after the culture, the medium is removed, 0.1 mL of saline containing 0.25% trypsin/phosphate buffer (hereinafter PBS) is added, left at room temperature for 5 minutes, then a culture supernatant is removed, and washing is performed.

(3) 0.1 mL of the medium is added thereto, and mixed with 0.1 mL of 80% Percoll (Pharmacia) to prepare 40% Percoll solution. This is overlaid on 0.1 mL of 70% Percoll placed in a 1.5 mL of a sample tube, and centrifuged (8,000 rpm, 10 minutes).

(4) After the centrifugation, cells present at an interface are collected, and after washing the cells with PBS, 1 mL of the medium is added. Polystyrene latex particles (FITC-PSLP) with particle diameter of 2.0 μm labeled with fluorescein isothiocyanate (FITC) at $1 \times 10^7$ are added, and a mixture is cultured for one hour. Labeling with fluorescent FITC is for easily performing quantitative analysis.

(5) After the culture, the centrifugation (700 rpm, 5 minutes) is performed, then 1 mL of PBS is added to macrophages in a precipitated layer, and the centrifugation is repeated twice.

(6) After removing PBS, 0.1 mL of 10% formalin/PBS is added to the cells, fixed for 5 minutes, then 1 mL of distilled water is added, the supernatant is removed, 1 mL of distilled water is added again, and the supernatant is removed. After removing the supernatant, 0.1 mL of distilled water is added to suspend the cells, and 0.02 mL of the suspension is taken, spread on a slide glass and dried.

(7) Under a fluorescent microscope, multiple visual fields are photographed, and a number of NR8383 cells which have incorporated FITC-PSLP per 100 cells is measured.

(8) A change of FITC-PSLP phagocytosed amounts in the macrophages by the PLGA fine particle formulation is as shown in Table 1. A low amount addition of the PLGA fine particle formulation does not remarkably affect the phagocytic capacity of the macrophages, but it is evident that the addition of 0.4 (μg/mL) noticeably activates the phagocytic capacity.

TABLE 1

Enhancement effect of PLGA fine particle formulation on phagocytic capacity of macrophages

| Amount of PLGA fine particle formulation (μg/mL) | Uptake rate of FITC-PSLP (%) |
|---|---|
| 0 | 11.6 |
| 0.004 | 8.8 |
| 0.04 | 12.3 |
| 0.4 | 20.2 |

II. Enhancement of Phagocytic Capacity of Macrophages by Lipopolysaccharide
1. Method of Preparing Lipopolysaccharide
(a) Material
(1) *Pantoea agglomerans* belonging to gram negative bacterium, genus *Pantoea*
(b) Preparation of Lipopolysaccharide
(1) *Pantoea agglomerans* is added to 7 liters of bouillon (10 g/L of tryptone, 5 g/L of yeast extract, 10 g/L of NaCl, 1 g/L of glucose, pH 7.5), cultured with shaking at 35° C. for 24 hours, and about 70 g of wet bacterial body is collected.

(2) 70 g of the bacterial body was suspended in 500 mL of distilled water, 500 mL of 90% heat phenol was added, stirred at 65 to 70° C. for 20 minutes, cooled, and then an aqueous layer was collected. The collected aqueous layer is dialyzed overnight to eliminate phenol, and an internal solution of the dialysis is ultrafiltrated to concentrate by a molecular weight 200,000 cutoff membrane under nitrogen gas at two atmospheres.

(3) A resulting crude frozen/dried lipopolysaccharide is dissolved in distilled water, applied on an anion exchange chromatography (supplied from Pharmacia, Q-Sepharose Fast Flow), a sample solution is passed through a column using a buffer containing 10 mM of Tris-HCl (pH 7.5) and 10 mM of NaCl, and a Limulus activity fraction is eluted with 200 to 400 mM of NaCl/10 mM Tris-HCl (pH 7.5). By ultrafiltrating this eluted solution, desalting, concentrating and freezing/drying under the same condition as the above, it is possible to yield about 300 mg of purified lipopolysaccharide from about 70 g of the wet bacterial body.

2. Enhancement Effect on Alveolar Macrophage Phagocytosis by Lipopolysaccharide (1) Alveolar macrophage cells (NR8383) are prepared at $1 \times 10^6$ cells/mL in a medium (Ham F-12K, 15% fetal calf serum), and added to a 24-well plate. Lipopolysaccharide is added thereto to become 1 μg/mL, and the culture is performed in a carbon dioxide gas incubator (37° C.).

(2) After culturing for one hour, the cells are transferred to a 1.5 mL sample tube, and the medium is eliminated by centrifugation (2,000 rpm, 5 minutes). Subsequently, 0.1 mL of 0.25% trypsin/PBS is added, the tube is left at room temperature for 5 minutes, then, a culture supernatant is eliminated by centrifugation (2,000 rpm, 5 minutes), and washing with PBS is performed.

(3) Thereto, 0.1 mL of the medium is added, and mixed with 0.1 mL of 60% Percoll to prepare 30% Percoll solution, which is then centrifuged (8,000 rpm, 10 minutes).

(4) After the centrifugation, the cells present on the liquid surface are collected, and washed twice with PBS. Subsequently, 1 mL of the medium is added, FITC-PSLP with a particle diameter of 2.0 μm at $1 \times 10^7$ is added, which is then cultured for one hour.

(5) After the culture, the supernatant is removed, 0.1 mL of 0.25% trypsin/PBS is added, and a mixture is left at room temperature for 5 minutes. Subsequently, 1 mL of the medium is added and then the centrifugation (700 rpm, 5 minutes) is performed.

(6) 1 mL of PBS is added to macrophages in a precipitated layer, the centrifugation (700 rpm, 5 minutes) is performed, and the supernatant is removed. Again 1 mL of PBS is added, the centrifugation (700 rpm, 5 minutes) is performed and the supernatant is removed.

(7) After removing the supernatant, 0.1 mL of 10% formalin/PBS is added to the cells, is fixed for 5 minutes, then 1 mL of distilled water is added, the supernatant is removed, 1 mL of distilled water is added again, and the supernatant is removed.

(8) After removing the supernatant, 0.1 mL of distilled water is added to suspend the cells, 0.02 mL of the suspension is taken, spread on a slide glass, and dried.

(9) Under a fluorescent microscope, multiple visual fields are photographed, and the number of NR8383 cells which have incorporated FITC-PSLP per 500 cells is measured.

(10) The increase of the FITC-PSLP-phagocytosed amount of the macrophages by the lipopolysaccharide is as shown in Table 2. It is evident that the phagocytic capacity of the macrophages is activated by the lipopolysaccharide.

TABLE 2

Activation of macrophage phagocytic capacity by lipopolysaccharide

| Addition amount of lipopolysaccharide (μg/mL) | Uptake rate of FITC-PSLP (%) |
|---|---|
| 0 | 31 |
| 1.0 | 51 |

B. Remedy which Acts Upon Pathogens in Macrophages

Effective migration of rifampicin (antituberculous drug) into macrophages by phagocytosing RFP-PLGA fine particle formation.

1. Preparation of PLGA Fine Particle Formation which Internally Includes Rifampicin (a) Materials (1) PLGA [poly(lactic acid/glycolic acid)copolymer] monomer ratio: 75:25 or 50:50, molecular weight: 5,000, 10,000 or 20,000, Wako Pure Chemical Industries Ltd., PLGA-5005, 5010, 5020, 7505, 7510, 7520.

(2) Rifampicin (3) PVA (polyvinyl alcohol) polymerization degree: 500.

(b) Preparation of RFP-PLGA Fine Particle Formation (1) PLGA (500 mg) and rifampicin (0, 50, 100 or 200 mg) are dissolved in 1.5 mL of methylene chloride.

(2) PVA is dissolved in water to become 0.3% (w/v).

(3) When 8 mL of a PVA aqueous solution of (2) is added to a solution of (1) and stirred for 3 minutes, an o/w type emulsion is formed.

(4) (3) is added into 200 mL of a PVA aqueous solution of (2), and stirred at room temperature at 520 rpm for 3 hours.

(5) A fine particle formulation is precipitated by centrifugation (3,000 rpm, 15 minutes), separated, and further washed twice by adding 10 mL of distilled water using a centrifuge.

(6) Drying under reduced pressure in a desiccator for 24 hours.

(7) The produced PLGA fine particles (molecular weight and composition) are correctly shown below.

1. RFP-PLGA 5005 (PLGA, molecular weight: 5,000; lactic acid/glycolic acid: 50:50).

2. RFP-PLGA 5010 (PLGA, molecular weight: 10,000; lactic acid/glycolic acid: 50:50).

3. RFP-PLGA 5020 (PLGA, molecular weight: 20,000; lactic acid/glycolic acid: 50:50).

4. RFP-PLGA 7505 (PLGA, molecular weight: 5,000; lactic acid/glycolic acid: 75:25).

5. RFP-PLGA 7510 (PLGA, molecular weight: 10,000; lactic acid/glycolic acid: 75:25).

6. RFP-PLGA 7520 (PLGA, molecular weight: 20,000; lactic acid/glycolic acid: 75:25).

The particle size distribution and the characteristics of all resulting fine particle formulations were the same as those of the fine particle formulations of PLGA alone (A. I. 1. (b) (7)).

(8) The fine particle formation of 4 mg where 0, 50, 100 or 200 mg of rifampicin is contained in 500 mg of PLGA is dissolved in 1 mL of methylene chloride, and subsequently an absorbance at 475 nm is measured by a spectrophotometer.

(9) Amounts of rifampicin recovered in RFP-PLGA fine particle formation (fine particle PLGA-7520 made up of PLGA molecular weight of 20,000 and lactic acid/glycolic acid of 75/25) are shown in Table 3. As is evident from this result, it is found that rifampicin has been efficiently formulated.

TABLE 3

Amounts of rifampicin internally included in RFP-PLGA fine particle formulation

| Rifampicin (mg) | Amount of PLGA (mg) | Rifampicin internally included (%) |
|---|---|---|
| 0 | 500 | — |
| 50 | 500 | 83 |
| 100 | 500 | 82 |
| 200 | 500 | 89 |

2. Other Method for Preparing RFP-PLGA Fine Particle Formation (Membrane Emulsification Method, Known in the Art)

Using a membrane emulsification method, the RFP-PLGA 7510 fine particle formation was prepared.

The membrane emulsification method is an emulsification method where one (dispersion phase) of two kinds of liquids which do not blend together is pressed to disperse in another liquid (continuous phase) through a porous glass membrane. By the use of this method, it is possible to obtain an emulsion with uniform particle diameters.

(a) Materials (1) PLGA [poly(lactic acid/glycolic acid)copolymer] monomer ratio: 75:25, molecular weight: 10,000, Wako Pure Chemical Industries Ltd., PLGA 7510.

(2) Rifampicin (3) PVA (polyvinyl alcohol) polymerization degree: 500

(b) Preparation of RFP-PLGA Fine Particle Formation (1) PLGA 500 mg and rifampicin 100 mg are dissolved in 10 mL of methylene chloride.

(2) PVA is dissolved in water to become 0.3% (w/v).

(3) When a solution of (1) is dispersed in 100 mL of PVA aqueous solution of (2) through an SPG membrane (Ise Chemicals Corporation, thin pore size: 0.49 μm), an oil-in-water (o/w type) emulsion is formed.

(4) (3) is added into 200 mL of PVA aqueous solution of (2), and stirred at room temperature at 520 rpm for 3 hours.

(5) A fine particle formulation is precipitated by centrifugation (3,000 rpm, 15 minutes), separated, and further washed twice by adding 10 mL of distilled water using a centrifuge.

(6) Drying under reduced pressure in a desiccator for 24 hours.

(7) An average particle diameter of the resulting fine particle formulation is 1.98 μm. A yield of PLGA calculated from PLGA (500 mg) used for the preparation and an entire weight of the recovered formulation was about 90%. The yield of rifampicin was about 75%. This particle is a solid at ambient temperatures.

3. Other Examples by Membrane Emulsification Method

The RFP-PLGA fine particles (molecular weight and composition) other than RFP-PLGA 7510 fine particle formulation were collectively shown below.

1. RFP-PLGA 5005 (PLGA molecular weight: 5,000; lactic acid/glycolic acid 50:50)

2. RFP-PLGA 5010 (PLGA molecular weight: 10,000; lactic acid/glycolic acid 50:50)

3. RFP-PLGA 5020 (PLGA molecular weight: 20,000; lactic acid/glycolic acid 50:50)

4. RFP-PLGA 7505 (PLGA molecular weight: 5,000; lactic acid/glycolic acid 75:25)

5. RFP-PLGA 7520 (PLGA molecular weight: 20,000; lactic acid/glycolic acid 75:25)

The method for preparing these RFP-PLGA fine particle formulations is the same as the above membrane emulsification method except kinds of PLGA.

The average particle diameters of the resulting fine particle formulations are 2.20 μm in PLGA 5005, 2.66 μm in PLGA 5010, 2.29 μm in PLGA 5020, 2.00 μm in PLGA 7505, and 1.85 μm in PLGA 7520. All yields of PLGA calculated from PLGA (500 mg) used for the preparation and an entire weight of the recovered formulation were about 90%. The yields of rifampicin were about 87% in PLGA 5005, about 78% in PLGA 5010, about 67% in PLGA 5020, about 91% in PLGA 7505, and about 58% in PLGA 7520.

4. Release of Rifampicin from RFP-PLGA Fine Particles (1) Respective RFP-PLGA fine particles (50 mg) prepared by the membrane emulsification method were dispersed in 5 mL of phosphate buffer at pH 7.4 (ionic strength: 0.154 M) retained at 37° C. (temperature).

(2) The supernatants were collected over time by the centrifugation, and 5 mL of the phosphate buffer at pH 7.4 (ionic strength: 0.154 M) was added to the remaining fine particles.

(3) A concentration eluted in the supernatant was measured. The measurement was performed using a spectrophotometer at a wavelength of 475 nm.

(4) Rates of rifampicin released from respective RFP-PLGA fine particles into the supernatant are shown in FIG. 4 and FIG. 5. From data of the present experiment, it was shown that releasing rates of rifampicin from PLGA with molecular weights of 5,000 and 10,000, i.e., PLGA 5005, PLGA 5010, PLGA 7505 and PLGA 7510 were fast. From these results, it has been shown that the PLGA compositions in which the molecular weight is 5,000 to 10,000 and the ratio of lactic acid to glycolic acid is 50:50 or 75:25 are excellent in migration of the drug into the macrophages via the phagocytosis.

5. Selective Increase of Intracellular Rifampicin Concentration by Phagocytosis of RFP-PLGA Fine Particle Formulation (PLGA-7520)

(1) The prepared RFP-PLGA fine particle formulation is dispersed again in PBS, the centrifugation (400 rpm, 5 minutes) is performed to eliminate large particles, and the fine particle formulation (about 30% in weight) prepared in sizes of about 1 to 3 μm by microscope observation are used for the following experiments.

(2) Cultured NR8383 cells at $5\times10^5$ cells/0.9 mL in a medium are placed in a 24-well plate, 0.12 mg/0.1 mL of each RFP-PLGA fine particle formulation is added thereto, and cultured for 12 hours.

(3) After the culture, the medium is removed, 0.1 mL of 0.25% trypsin/PBS is added, then left at room temperature for 5 minutes, subsequently the culture supernatant is removed and the washing is performed.

(4) 0.1 mL of the medium is added thereto, and mixed with 0.1 mL of 80% Percoll to prepare 40% Percoll solution. This is overlaid on 0.1 mL of 70% Percoll placed in a 1.5 mL of a sample tube, and centrifuged (8,000 rpm, 10 minutes).

(5) After the centrifugation, cells present at an interface are collected, washed with PBS, and subsequently rifampicin incorporated in the cells is extracted with methylene chloride.

(6) An amount of rifampicin is determined from an absorbance at 475 nm.

(7) As a control, a dimethylsulfoxide (DMSO) solution of rifampicin at the same amount as that contained 0.12 mg of the RFP-PLGA fine particle formulation is prepared, this is added to a 24-well plate to which 1 mL of the medium is added, and NR8383 cells are added thereto.

(8) The cells are cultured for 12 hours, subsequently the cells ($5\times10^5$ cells) are collected, and rifampicin in the cells is extracted with methylene chloride.

Figure 3:
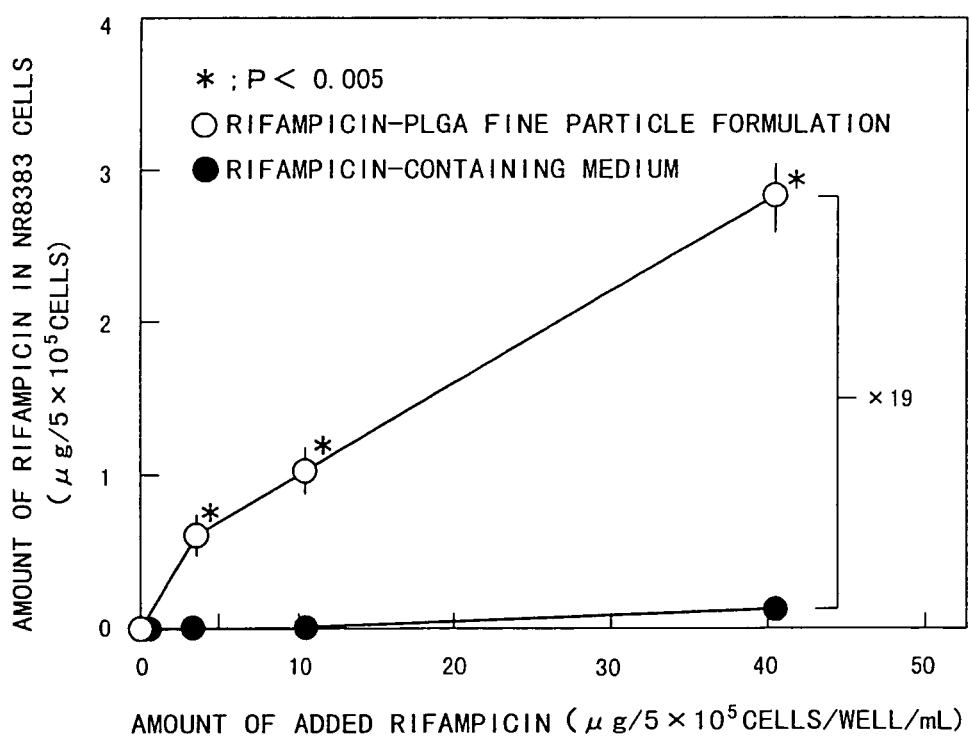
FIG. 3 is a view illustrating by comparison how much amounts incorporated in NR8383 cells are different by administering rifampicin according to the invention and by administering it using a solution conventionally used.

(9) Uptake amounts of rifampicin by the macrophages are shown in FIG. 3. It is shown that rifampicin at about 19 times is incorporated in the addition amount of 40 (μg/$5\times10^5$ cells/well/mL) of rifampicin in the case of the present RFP-PLGA fine particle formulation compared to the conventional medium containing rifampicin.

C. Medicament (A+B) which Enhances Phagocytic Capacity of Macrophages and Acts Upon Pathogens in Macrophages Enhancement Effect on Phagocytic Activity of Macrophages by Phagocytosing RFP-PLGA Fine Particle Formulation 1. Preparation of RFP-PLGA Fine Particle Formulation (a) Materials (1) PLGA [poly(lactic acid/glycolic acid)copolymer] monomer ratio: 75:25 or 50:50, molecular weight: 5,000, 10,000 or 20,000, Wako Pure Chemical Industries Ltd., PLGA-5005, 5010, 5020, 7505, 7510, 7520.

(2) Rifampicin (3) PVA (polyvinyl alcohol) polymerization degree: 500

(b) Preparation of RFP-PLGA Fine Particle Formulation (1) PLGA 500 mg and rifampicin 100 mg are dissolved in 1.5 mL of methylene chloride.

(2) PVA is dissolved in water to become 0.3% (w/v).

(3) When 8 mL of a PVA aqueous solution of (2) is added to a solution of (1) and stirred for 3 minutes, an o/w type emulsion is formed.

(4) (3) is added into 200 mL of a PVA aqueous solution of (2), and stirred at room temperature at 520 rpm for 3 hours.

(5) A fine particle formulation is precipitated by centrifugation (3,000 rpm, 15 minutes), separated, and further washed twice by adding 10 mL of distilled water using a centrifuge.

(6) Drying under reduced pressure in a desiccator for 24 hours.

(7) The particle size distribution and the characteristics of the resulting fine particle formulations were the same as those of the fine particle formulations of PLGA alone (A. I. 1. (a) (7)).

(8) The fine particle formulation is dispersed again in PBS, the centrifugation (400 rpm, 5 minutes) is performed to eliminate large fine particle formulation, and the fine particle formulation prepared in sizes of about 1 to 3 μm is used for the following experiments.

2. Enhancement of Macrophage Phagocytic Activity by Phagocytosing RFP-PLGA Fine Particle (PLGA-7520) Formulation (1) Alveolar macrophage cells (NR8383) are prepared at $1\times10^6$ cells/mL in a medium (Ham F-12K, 15% fetal calf serum), added in a 24-well plate, and 0.012, 0.12 or 1.2 μg of PLGA fine particle formulation is added thereto, which is then cultured in a carbon dioxide gas incubator (37° C.).

(2) One hour after the culture, the cells are transferred to 1.5 mL of a sample tube, the medium is removed, 0.1 mL of 0.25% trypsin/PBS is added, a mixture is left at room temperature for 5 minutes, then the culture supernatant is removed, and washing is performed.

(3) Thereto, 0.1 mL of the medium and 0.1 mL of 90% Percoll are added to make 45% Percoll, and subsequently the centrifugation (8,000 rpm, 10 minutes) is performed.

(4) After the centrifugation, the cells present on the liquid surface are collected, and washed twice with PBS. Subsequently, 1 mL of the same medium as that used in (1) is added, FITC-PSLP with a particle diameter of 2.0 μm at $1\times10^7$ is added, which is then cultured for one hour.

(5) After the culture, the supernatant is removed, 0.1 mL of 0.25% trypsin/PBS is added, and a mixture is left at room temperature for 5 minutes. Subsequently, 1 mL of the medium is added and then the centrifugation (700 rpm, 5 minutes) is performed.

(6) 1 mL of PBS is added to macrophages in a precipitated layer, the centrifugation (700 rpm, 5 minutes) is performed, and the supernatant is removed. Again 1 mL of PBS is added, the centrifugation (700 rpm, 5 minutes) is performed and the supernatant is removed.

(7) After removing the supernatant, 0.1 mL of 10% formalin/PBS is added to the cells, is fixed for 5 minutes, then 1 mL of distilled water is added, and then the centrifugation (700 rpm, 5 minutes) is performed, 1 mL of distilled water is added again, and the supernatant is removed. Thereto, 0.1 mL of distilled water is added to suspend the cells, 0.02 mL of the suspension is taken, spread on a slide glass, and dried.

(8) Under a fluorescent microscope, multiple visual fields are photographed, and the number of the macrophages (NR8383 cells) which have incorporated FITC-PSLP per 500 cells is measured.

(9) The increase of FITC-PSLP amounts phagocytosed by the macrophages due to phagocytosis of RFP-PLGA fine particle formulation is as shown in Table 4. It is evident that the phagocytic capacity of the macrophages is activated by the RFP-PLGA fine particle formulation.

TABLE 4

Enhancement effect on phagocytosis of FITC-PSLP by NR8383 cells which have phagocytosed the RFP-PLGA fine particle formulation

| Amount of RFP-PLGA fine particle formulation (μg/mL) | Uptake rate of FITC-PSLP (%) |
| --- | --- |
| 0 | 31 |
| 0.012 | 45 |
| 0.12 | 47 |
| 1.2 | 52 |

From the above results, (1) it has been demonstrated that the PLGA fine particle formulation and lipopolysaccharide activate the phagocytic capacity of the macrophages. Also, it has been demonstrated (2) that the migration of rifampicin into the macrophages is remarkably increased by being internally included in the PLGA fine particle formulation, and (3) that the phagocytic capacity of the macrophages is activated even when rifampicin is contained in the PLGA fine particle formulation. Therefore, the rifampicin-containing PLGA fine particle formulation activates the phagocytic capacity of the macrophages resulting in the increased rifampicin concentration in the macrophages, and thus makes it possible to accomplish the object of the invention to efficiently affect against the pathogens retained in the macrophages. The above results indicate one example of the novel remedy where the remedy which acts upon the pathogens in the macrophages is effectively incorporated in the macrophages by "facilitating the phagocytic activity of the macrophages" which is a basic concept of the invention.

3. Exterminating Effect on Tuberculosis Germs in Macrophages by Phagocytosing RFP-PLGA Fine Particle Formulation (a) Method of Measuring Viability of Tuberculosis Germs (BCG) in Macrophages (1) Dried BCG vaccine was dissolved in saline (12 mg/mL), stirred, subsequently KRD medium (3 to 4 mL) was transferred to a T-25 culture flask, then 40 μL of a BCG suspension was added thereto, and cultured in a dry incubator at 37° C.

(2) In the experiment, a bacterial solution and glass beads were placed at a ratio of 1:4 in a sample tube, which was then stirred for one minute by a vortex mixer. Subsequently, the bacterial body was dispersed by sonication for 5 minutes using an ultrasonic washer.

(3) NR8383 cells at a concentration of $1\times10^6$ cells/mL were placed in a 6-well plate (total volume 5 mL). The tuberculosis germs (BCG) at 10 per cell (multiplicity of infection (MOI)=10) were added to a cell culture medium.

(4) After infecting at 37° C. in a carbon dioxide gas incubator for 4 hours, the centrifugation at 2,000 rpm for 5 minutes (SCT15B) was performed, and then the supernatant was removed. Using a serum free medium, likewise the centrifugation was repeated twice to eliminate bacteria present out of the cells.

(5) NR8383 cells at a concentration of $1\times10^6$ cells/mL were seeded in a 24-well plate.

(6) Respective RFP-PLGA fine particles at 10 per cell were added to the culture medium of NR8383 cells.

(7) After phagocytosing at 37° C. in the carbon dioxide gas incubator for 4 hours, the particles present out of the cells were eliminated using 25% trypsin.

(8) 80% Percoll was added to make 40% Percoll-cell solution, and further 70% Percoll was added to make a density gradient. After the centrifugation (SORVALL Biofuge Fresco) at 10,000 rpm for 5 minutes, the cells at an interface between 40% and 70% Percoll were collected to separate the cells from RFP-PLGA.

(9) Using PBS, likewise the centrifugation was repeated twice to eliminate Percoll.

(10) Rates of living bacteria and dead bacteria were measured using a staining method for fluorescein diacetate (FDA)/ethidium bromide (EB). FDA was dissolved in acetone at a concentration of 5 mg/mL, and 20 μl thereof was diluted with 1 mL of PBS at use. EB was dissolved in PBS at a concentration of 20 μg/mL, and 50 μl thereof was diluted with 1 mL of PBS at use. Equal amounts of diluted FDA and EB were mixed and used for staining. This mixed solution (1 μL) was placed on a slide glass, 1 μL of the bacterial solution was placed thereon, which was then left at room temperature for 2 minutes and observed under a fluorescent microscope. In the living bacteria, FDA is decomposed by esterase activity derived from the bacteria to emit fluorescence with a green color. On the other hand, in the dead bacteria, there is no esterase activity, therefore, staining with FDA is not observed, and the bacteria are stained with EB to emit fluorescence with an orange color.

(b) Exterminating Effect of RFP-PLGA Fine Particle Formulation Incorporated in Macrophages by Phagocytosis on Tuberculosis Germs (1) In order to examine an exterminating effect on tuberculosis germs in the macrophages by RFP-PLGA fine particle, the RFP-PLGA fine particles were administered to the macrophages (macrophages infected with tuberculosis germs) which have previously phagocytosed the tuberculosis germs, and these fine particles were phagocytosed by the macrophages.

Figure 6:
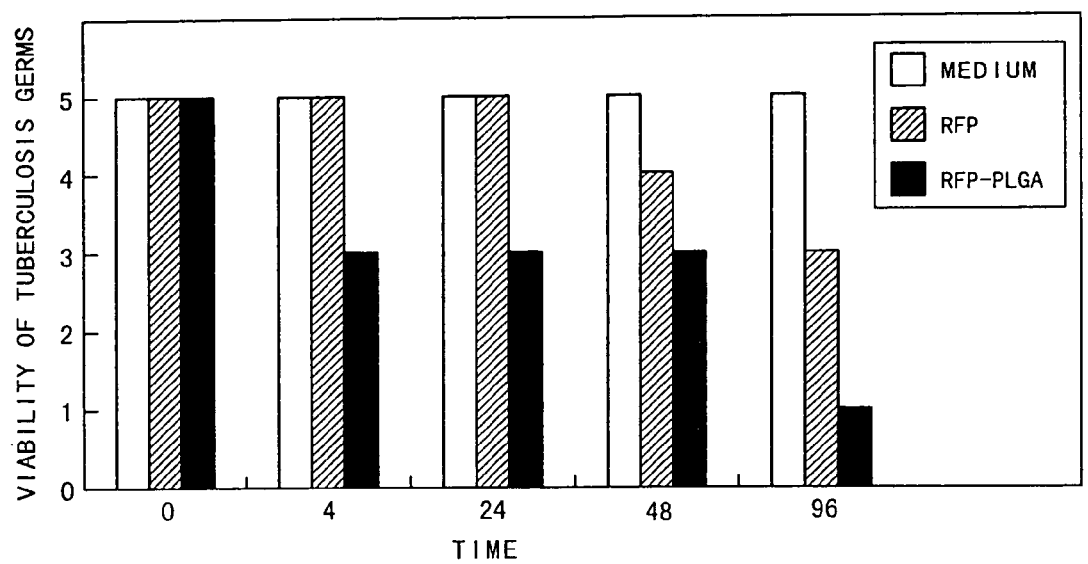
FIG. 6 is a view illustrating that tuberculosis germs in the macrophages can be exterminated by phagocytosis of RFP-PLGA particles by the macrophages which have phagocytosed the tuberculosis germs. Viability was evaluated by ranking as follows: 1: 5% or less, 2: 5 to 25%, 3: 25 to 50%, 4: 50 to 75%, and 5: 75% or more. An amount of administered rifampicin is 100 µg/mL in a single administration (indicated by RFP in the figure) or 5 µg/mL (estimated value) in the administration by RFP-PLGA (indicated by RFP-PLGA in the figure).

(2) The results of examining how exterminating effects RFP-PLGA which migrated in the macrophages by the phagocytosis exhibited against the tuberculosis germs in the macrophages are shown in FIG. 6. It is evident that the intracellular concentration of rifampicin is significantly higher in the dosage of RFP-PLGA fine particles containing rifampicin of about one twentieth (MOI=10, an estimated rifampicin amount is 5 μg/mL, and thus rifampicin in the fine particle formulation corresponds to one twentieth of the amount in the case of administering rifampicin alone) than in the dosage of rifampicin alone (100 μg/mL). The administration of the RFP-PLGA fine particles to the alveolar macrophages infected with tuberculosis germs exterminated the tuberculosis germs in the cells at an efficiency of 20 times or more compared to the administration of rifampicin alone. That is, by administrating the drug via the phagocytosis of the particles, a treatment coefficient was improved by 20 times or more regardless of the antituberculous effect of the drug per se.

Provision of Remedy which Facilitates Phagocytic Activity of Macrophages and Acts Upon Macrophages in Dysfunctional State It has been known that typically numerous macrophages infiltrate in cancer tissues. This is based on the fact that because cancer cells are foreign substances for a living body, the macrophages are accumulated for the purpose of eliminating the cancer cells. If the macrophages work normally, the cancer cells are injured and vanish. However, if the macrophages function abnormally, the cancer cells cannot be injured, grow and results in the formation of a tumor mass. As described already, by activating the macrophages, it becomes possible to also injure the cancer cells. Therefore, by facilitating the phagocytic activity of the macrophages, it is possible to make the macrophages with dysfunction acquire a cytotoxic effect on the cancer cells, and to effectively treat the cancer.

On the other hand, as shown in Table 2, the phagocytosis by the alveolar macrophages was enhanced by 166% by the treatment with lipopolysaccharide (1 µg/mL), and the alveolar macrophages were activated by the lipopolysaccharide. Thus, it appears that the alveolar macrophages whose phagocytic capacity has been activated by the lipopolysaccharide elicit the cytotoxic effect on lung cancer cells. Therefore, here, an example of the cytotoxic effect on lung cancer cells of the alveolar macrophages activated by the lipopolysaccharide is shown.

Specific Application Example

Lung Cancer

The cytotoxic effect on lung cancer cells by activating the alveolar macrophages is shown as the application example.

1. Activation of Alveolar Macrophages by Lipopolysaccharide and Co-Culture of Alveolar Macrophages with Sato Lung Cancer Cells (1) NR8383 cells at a concentration of $1 \times 10^6$ cells/mL were placed in a 24-well plate (total volume: 1.5 mL). As the control, 5% fetal calf serum, 150 µl of F-12K medium, and 150 µl of 10 µg/mL lipopolysaccharide were added.

(2) The cells were left in the carbon dioxide gas incubator at 37° C. for 24 hours.

(3) Sato lung cancer cells were prepared at a concentration of $1 \times 10^5$ cells/mL, and 50 µl per well was added in a 96-well plate.

(4) NR8383 cells treated in the section (1) were prepared at concentrations of $5 \times 10^5$, $1 \times 10^5$, $5 \times 10^4$ and $1 \times 10^4$ cells/mL, and 50 µl per well was added to the 96-well plate (total volume: 100 µl).

(5) The cells were left in the carbon dioxide gas incubator at 37° C. for 4 hours.

2. Cytotoxic Effect of Macrophages Co-Cultured with Sato Lung Cancer Cells on Lung Cancer Cells (1) The cytotoxic effect of the macrophages activated by lipopolysaccharide described in 1 and co-cultured with Sato lung cancer cells on lung cancer cells was evaluated from amounts of lactate dehydrogenase released from the cells into the medium. Therefore, the plate was centrifuged at 1,000 rpm for 5 minutes, and 50 µl of the supernatant was transferred to another 96-well plate.

(2) Subsequently, 50 µl of a substrate solution attached to a kit (CytoTox 96 Non-radioactive cytotoxicity assay, Promega, cat. G1780) for measuring the amounts of lactate dehydrogenase was added. As a positive control, a lactate dehydrogenase enzyme dilution liquid (5000 times dilution liquid, 50 µl) attached to the kit was used.

(3) The plate was shielded from light with aluminium foil, and left at room temperature for 30 minutes.

(4) The reaction was stopped by adding 50 µl of a stopping liquid.

(5) An absorbance at 495 nm was measured using a microplate reader (Model 550, Bio-Rad).

(6) Cytotoxicity (%) was calculated from each absorbance.

(7) The cytotoxic effect of NR8383 on Sato lung cancer cells is shown in FIG. 7. It has been shown that the phagocytosis by NR8383 treated with lipopolysaccharide is facilitated compared to NR8383 without treatment with lipopolysaccharide and consequently the cytotoxic effect on Sato lung cancer is enhanced depending on cell ratios.

Provision of Remedy which Facilitates Phagocytic Activity of Macrophages and Leads Pathogen-Retaining Macrophages to Cell Death The remedy in the present embodiment mode is characterized in that the macrophages which retain the pathogens are led to cell death by facilitating the phagocytic activity of the macrophages.

As shown in Table 2, the lipopolysaccharide well-known as a macrophage activator facilitates the phagocytic activity of the macrophages. Also, interferon-y which is a representative cytokine of macrophage activating factors facilitates the phagocytic activity. That is, the facilitation of phagocytic activity of the macrophages is one of the indicators of the macrophage activation. It can be said that the facilitation of the phagocytic activity by the phagocytosis is the facilitation of macrophage activation which is the facilitation of phagocytosis by stimulation which is the phagocytosis. It has also been known that change of a membrane structure is induced in the macrophage and a membrane-bound tumor necrosis factor (TNF) is induced in the macrophage. Therefore, along with the macrophage activation by stimulation which is the phagocytosis, the membrane-bound TNF is induced.

AIDS occurs due to destruction of T cells by infection with the AIDS virus resulting in immunodeficiency. AIDS virus infects not only T cells but also macrophages. This infection initiates by adhesion of the virus to CD4 protein commonly expressed on T and macrophage cell membranes. The macrophage infected with the AIDS virus does not lead to the cell death, but produces the AIDS virus persistently, and becomes the infectious pathogen vehicle as described in detail in II. (2).

Therefore, if the macrophages infected with the AIDS virus can be led to cell death, the extermination of the infectious pathogen vehicles is accomplished. As one example capable of realizing this possibility, it is shown that the membrane-bound TNF can act upon the macrophage cells infected with the AIDS virus (HIV) to specifically lead the cells to cell death.

Specific Application Example

Induction of Death of Cells Infected with HIV by Membrane Bound TNF-Expressing Cells As an example where TNF induces cell death in the cells infected with pathogens, the effect of TNF on MOLT-4 cells infected with HIV is shown.

1. Production of Membrane Bound TNF-Expressing Cells (1) In order to stably express the membrane bound TNF, according to a previous report (Journal of Virology, Vol. 63, pp. 2504-2509, 1989), an expression plasmid (pMT2 β G/HuproTNF) for murine and human membrane bound TNF was made.

(2) Then, this plasmid was mixed with a plasmid for selection of transformants, in which a neomycin resistant gene is incorporated at a ratio of 10:1, and introduced into fibroblast cells (NIH3T3 cells) derived from murine embryo.

(3) The above NIH3T3 cells transformed were cultured in the presence of 800 μg/mL of neomycin which is a selection marker in the carbon dioxide gas incubator at 37° C. for about 2 weeks.

(4) After the culture, a clone of TNF incorporated in the cells was acquired.

(5) It was confirmed that the acquired clone expressed the membrane bound TNF by an enzyme immunoassay.

2. Preparation of MOLT-4 Cells Infected with HIV (1) For cells infected with HIV, MOLT-4 cells were infected in the medium (RPMI1640, adding 10% fetal calf serum, penicillin (100 U/mL), streptomycin (100 μg/mL)) in the carbon dioxide gas incubator at 37° C. according to the previous report (Journal of Virology, Vol. 63, pp. 2504-2509, 1989) using cells infected with HIV (HTLV-IIIB strain). When infection with the AIDS virus is established in MOLT-4 cells, MOLT-4 cells exhibit characteristics to persistently produce the AIDS virus. Therefore, with respect to the production of the AIDS virus, a MOLT-4 cell is a model of the macrophage infected with AIDS virus.

(2) In this infection condition, 90% or more of MOLT-4 cells infected with HIV became HIV antibody positive.

(3) Therefore, by the cells infected with HIV, HIV was introduced into almost all MOLT-4 cells, and MOLT-4 cells infected with HIV were prepared.

3. Induction of Cell Death of Cells Infected with HIV by Membrane Bound TNF-Expressing Cells.

(1) NIH3T3 cells where the plasmid of TNF had been introduced were semi-confluently cultured in a 24-well culture plate.

(2) Then, a certain amount of MOLT-4 cells infected with HIV was added and mixed/cultured in the carbon dioxide gas incubator at 37° C. for 3 days.

(3) In order to examine the effect of the expressed membrane bound TNF on the cells infected with HIV, the viability of the cells infected with HIV was measured by a trypan blue dye exclusion method.

(4) As a result, it was observed that cell death was induced in 40% of MOLT-4 cells infected with HIV by the mixed culture with the membrane bound TNF-expressing cells.

As is evident from the above example, it is evident that the membrane bound TNF induces specifically cell death in the cells infected with AIDS virus (HIV). From these phenomena, it can be seen that the macrophages led to dysfunction by retaining the pathogens are activated by phagocytosing the pathogens and consequently induced membrane bound TNF leads the macrophages infected with pathogens to cell death.

Diseases due to the retention of pathogens by macrophages include mycobacteriosis, AIDS, chlamydiosis or toxoplasmosis and the like. Mycobacteriosis includes tuberculosis whose causative pathogen is *Mycobacterium tuberculosis* or *Mycobacterium bovis*, lepra whose causative pathogen is *Mycobacterium leprae*, or atypical mycobacteriosis whose causative pathogen is *Mycobacterium avium* and the like, or the like. As causative pathogens of chlamydiosis, there are *Chlamydia pneumoniae, Chlamydia trachomatis, Chlamydia psittaci* and the like. The present invention can effectively apply to all of them. The exterminating effect of the RFP-PLGA fine particles on the tuberculosis germs in the macrophages shown in the present embodiment mode is not accomplished unless rifampicin is released from the RFP-PLGA fine particles incorporated in phagosomes by phagocytosis and at least two passages via intracellular vesicular membrane structures are possible where the rifampicin permeates the phagosome membrane and further permeates the phagosome membrane of the phagosome which contains the tuberculosis germs. Survival strategies of the causative pathogens shown above in the macrophages are diverse. In entire mycobacteriosis, *Legionella* and *Toxoplasma*, the causative pathogens are alive in the macrophages by surviving in the phagosomes. *Listeria* and *Chlamydia* have the characteristics that the causative pathogens evacuate from the phagosomes. This intracellular existence aspect of the causative pathogens is presumed to be more easily compared to a case where the causative pathogens exist in the phagosomes because the drug efficacy can be anticipated when the drug permeates the phagosome membrane once from the perspective of delivery of the drug. AIDS is similar to *Listeria* and the like in the aspect that drug efficacy can be anticipated if the drug is delivered to the causative pathogens present in the cells. From the above, the invention is a promising treatment for the causative pathogens described above.

Medicines for various diseases to which the invention can apply effectively are cited below.

1) Mycobacteriosis: rifampicin, isoniazid, ethambutol, pyrazinamide, azithromycin, kanamycin, streptomycin sulfate, enviomycin, ethioniamide, cycloserine, levofloxacin, diaphenylsulfone.

2) AIDS: azidothymidine, dideoxyinosine

3) Chlamydiosis: minocycline hydrochloride, doxycycline hydrochloride, clarithromycin, sparfloxacin, roxithromycin, levofloxacin.

4) Toxoplasmosis: pyrimethamine, sulfamonomethoxine, acetylspiramycin.

5) Malaria: chloroquine phosphate, quinine sulfate, sulfadoxine, mefloquine.

6) Cancer: 5-fluorouracil, adriamycin, cisplatin, etoposide, mitomycin, vincristine, taxol, camptothecin, vinblastine, cyclophosphamide, bleomycin.

7) Crohn's disease: salazosulfapyridine, glucocorticoid.

8) Rheumatoid: gold sodium thiomalate, penicillamine, bucillamine, glucocorticoid.

All publications, patents and patent applications are incorporated herein by reference by entirety.

INDUSTRIAL APPLICABILITY

According to the invention, it is possible to provide a remedy which can effectively treat a disease caused by macrophages with dysfunction or macrophages as vehicles.

The invention claimed is:

1. A remedy wherein phagocytic activity of macrophages is enhanced and all or a part of the pathogens present in the macrophages are exterminated, the remedy comprising:
particles, which are capable of being phagocytized by macrophages, with diameters of 1 to 6 μm made of PLGA (poly(lactic acid/glycolic acid) copolymer) with a molecular weight of 10,000 and a monomer ratio of lactic acid/glycolic acid of 50:50 to 75:25, the particles containing rifampicin, the particles containing a least one member selected from the group consisting of lipopolysaccharide and a medicament for treating a disease, and the particles containing PVA (polyvinyl alcohol).

* * * * *